(12) United States Patent
Maples

(10) Patent No.: US 7,476,102 B2
(45) Date of Patent: Jan. 13, 2009

(54) CONTAMINATION AVOIDING DEVICE

(76) Inventor: Paul D. Maples, 3198 Beachcomber Dr., Morro Bay, CA (US) 93442

( * ) Notice: Subject to any disclaimer, the term of this patent is extended or adjusted under 35 U.S.C. 154(b) by 0 days.

(21) Appl. No.: 11/449,963

(22) Filed: Jun. 9, 2006

(65) Prior Publication Data

US 2007/0283966 A1    Dec. 13, 2007

(51) Int. Cl.
*G09B 19/00* (2006.01)
(52) U.S. Cl. ................................. 434/247
(58) Field of Classification Search ........... 434/236, 434/247, 262, 274; 482/124; 600/300; 128/878, 128/881
See application file for complete search history.

(56) References Cited

U.S. PATENT DOCUMENTS

| | | | |
|---|---|---|---|
| 156,053 A | 10/1874 | Bryan | |
| 407,116 A | 7/1889 | Pratt | |
| 1,207,614 A | 12/1916 | Olds | |
| 1,772,601 A | 8/1930 | Dunham | |
| 2,106,658 A | 1/1938 | Rakos | |
| 2,667,350 A | 1/1954 | Wilson et al. | |
| 2,704,069 A * | 3/1955 | Donelan | 128/881 |
| 3,064,970 A | 11/1962 | Thompson | |
| 3,103,660 A | 9/1963 | Ticktin | |
| 3,482,580 A | 12/1969 | Hollabaugh | |
| 3,885,576 A | 5/1975 | Symmes | |
| 3,889,163 A | 6/1975 | Symmes | |
| 3,963,033 A * | 6/1976 | Pope | 131/270 |
| 4,189,712 A | 2/1980 | Lemelson | |
| 4,246,913 A | 1/1981 | Ogden et al. | |
| 4,440,160 A | 4/1984 | Fischell et al. | |
| 4,524,773 A * | 6/1985 | Fischell et al. | 607/58 |
| 4,682,155 A | 7/1987 | Shirley | |
| 4,684,933 A | 8/1987 | Dill | |
| 4,692,748 A | 9/1987 | Pinsak et al. | |
| 4,715,367 A | 12/1987 | Crossley | |
| 4,842,519 A | 6/1989 | Dworkin | |
| 4,965,553 A | 10/1990 | DelBiondo, II et al. | |
| 4,966,164 A | 10/1990 | Colsen et al. | |
| 5,123,425 A | 6/1992 | Shannon, Jr. et al. | |
| 5,218,344 A | 6/1993 | Ricketts | |
| 5,396,215 A | 3/1995 | Hinkle | |
| 5,477,867 A | 12/1995 | Balkanyi | |
| 5,509,426 A * | 4/1996 | Sowerby | 128/878 |
| 5,826,578 A * | 10/1998 | Curchod | 600/595 |
| 5,908,301 A | 6/1999 | Lutz | |
| 5,978,972 A | 11/1999 | Stewart et al. | |
| 6,093,158 A | 7/2000 | Morris | |
| 6,334,073 B1 | 12/2001 | Levine | |
| 6,413,190 B1 * | 7/2002 | Wood et al. | 482/8 |

(Continued)

*Primary Examiner*—Kurt Fernstrom
(74) *Attorney, Agent, or Firm*—Charmasson, Buchaca & Leach, LLP

(57) ABSTRACT

A device for minimizing the absorption of pathogens collected on a person's hands by contact between the hand and the face of said person, includes a barrier placed in the crook of the elbow that limits the flexion of the elbow as the hand approaches the face. In an alternate embodiment of the invention, a proximity sensor is positioned on a part of the person's body to sense and warn the person that a hand is about to touch the face. An audio or visual warning signal or a mechanical or electrical stimulation may be triggered by the output of the sensor. A method is also provided for progressively weaning the person from reliance on said devices.

13 Claims, 3 Drawing Sheets

U.S. PATENT DOCUMENTS

| | | | |
|---|---|---|---|
| 6,487,906 B1 * | 12/2002 | Hock | 73/379.01 |
| 6,567,785 B2 | 5/2003 | Clendenon | |
| 6,762,687 B2 * | 7/2004 | Perlman | 340/573.1 |
| 7,033,281 B2 * | 4/2006 | Carnahan et al. | 473/221 |
| 2002/0013612 A1 | 1/2002 | Whitehurst | |
| 2003/0040408 A1 * | 2/2003 | Cooper | 482/124 |
| 2005/0113652 A1 * | 5/2005 | Stark et al. | 600/300 |
| 2007/0163365 A1 * | 7/2007 | Reed | 73/862 |
| 2007/0191743 A1 * | 8/2007 | McBean et al. | 601/5 |

* cited by examiner

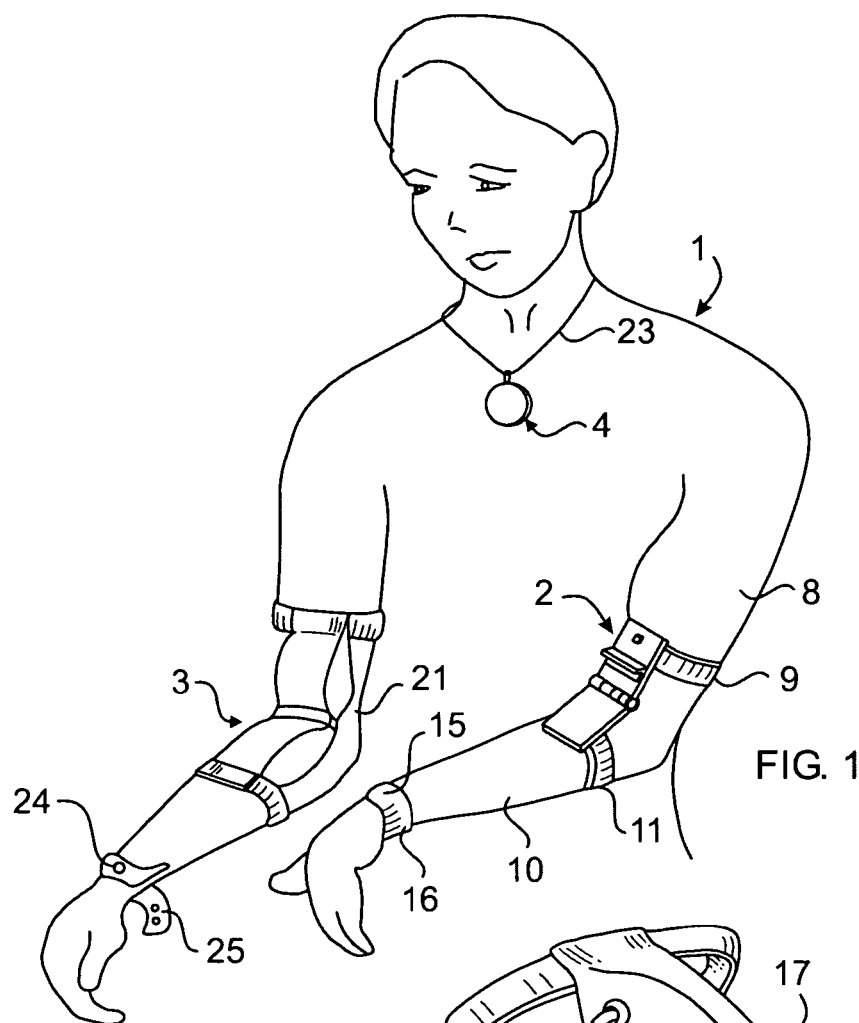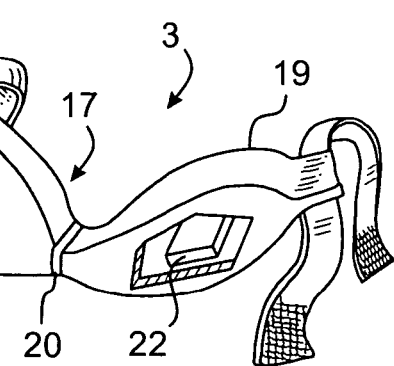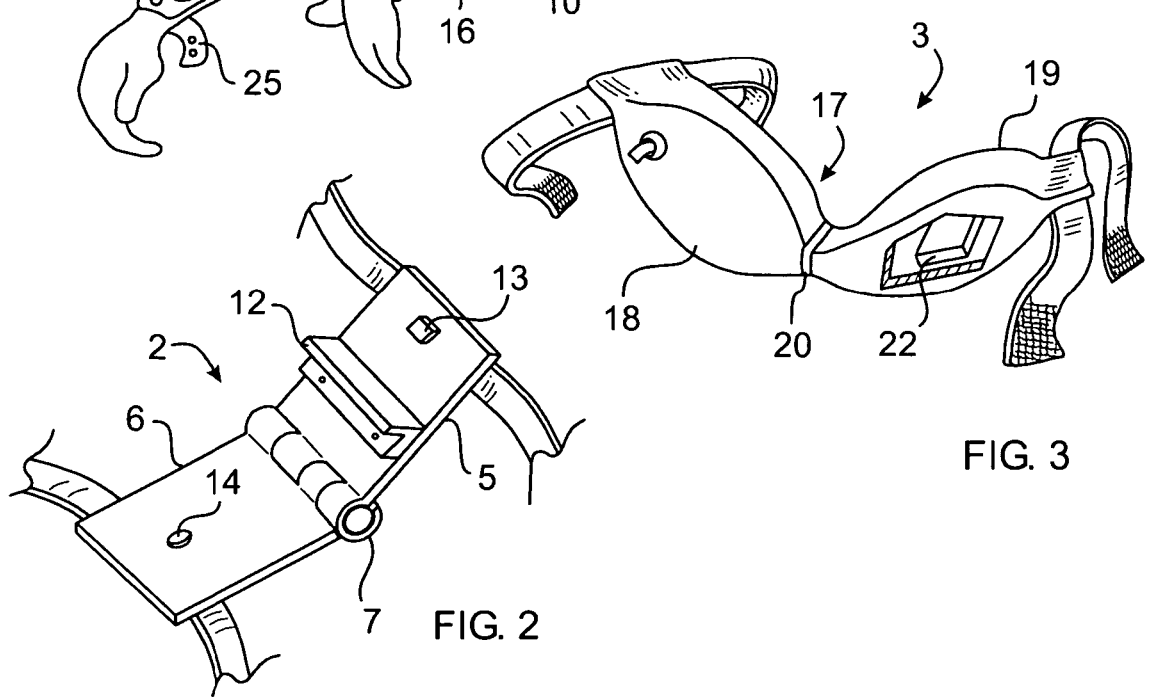

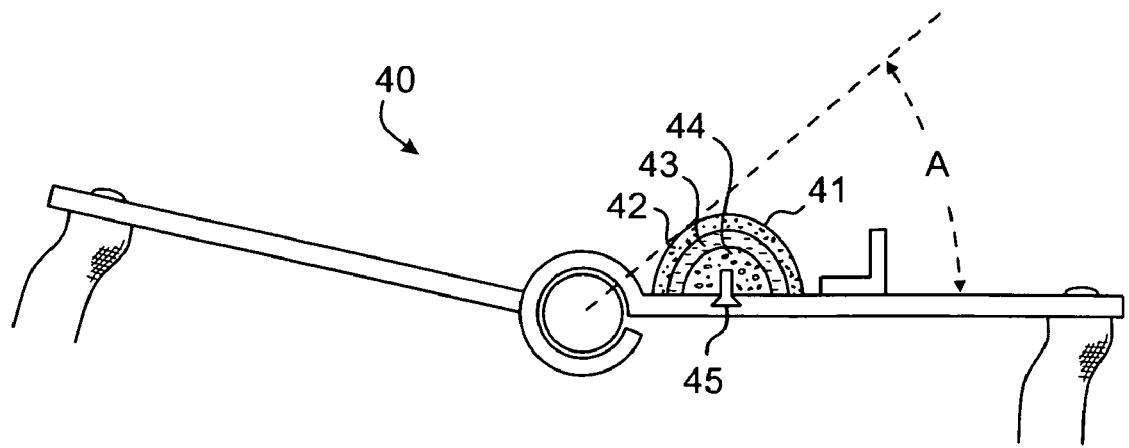
FIG. 4
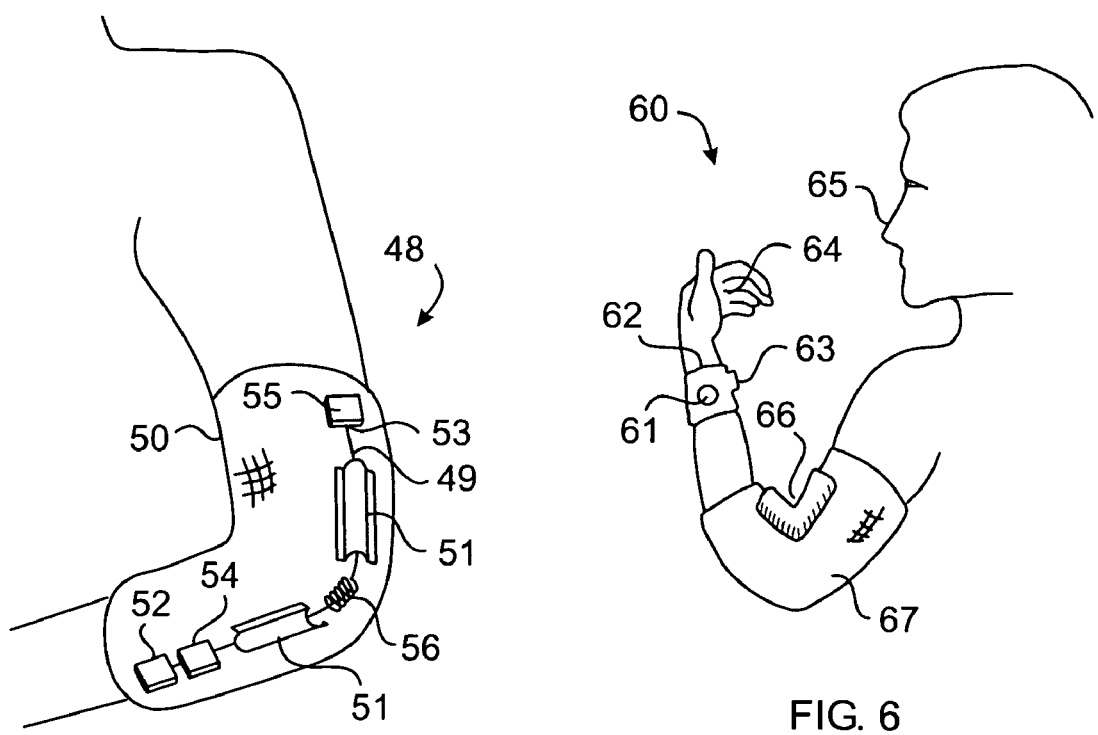
FIG. 5
FIG. 6

CONTAMINATION AVOIDING DEVICE

FIELD OF THE INVENTION

This invention relates generally to apparatuses for preventing or correcting certain behaviors and more specifically inadvertent transfer of infectious pathogens from the hand to the face where they can be easily absorbed through the nose, mouth or eyes.

BACKGROUND

It is well documented that one primary channel of infectious pathogen transfer from one person to another is the latter's touching an infected one or contacting a contaminated object, then touching his or her face with the now contaminated hand. Pathogens lying around the nose, eyes or mouth can be easily absorbed. The phenomenon is particularly common in connection with cold and flu viruses.

By the very nature of such interactions, it is virtually impossible to prevent contamination of the hands. The simple act of handling money, using restaurant flatware, or touching a door handle may result in the gathering of infectious pathogens.

Absorption of these pathogens through the eyes, nose or mouth can be limited by the wearing of goggles and face masks. However, those precautionary implements are cumbersome, can be aesthetically undesirable and can otherwise interfere with normal activities.

SUMMARY

The instant invention provides a practical way to minimize the absorption of pathogens collected on a person's hands by causing that person to be aware that his hand is about to touch his face, and by deterring the person from doing so. A foldable or compressible implement placed in the crook of the elbow tracks and either limits the range of flexion of the elbow, or provides a substantial resistence to such a flexion that brings the person's attention to the fact that the hand may be about to touch the face. The invention also proposes a variety of proximity sensors and indicators to that effect. A treatment method is also provided for training a person into avoiding contacting the face with one's hand. In a first phase, one of the most restrictive of the proposed devices such as the flexion limiting one is used over a period of time, as well as one of the warning indicators. In a second phase, a less forceful or conspicuous pressure or proximity detector reminds the person that he or she might be reverting to a compulsive habit of face touching.

Some embodiments provide a device for minimizing the absorption of pathogens by a person through contact of said person's face by one of said person's hands, which comprises means for limiting the range of movement of said hand toward said face. Some embodiments further comprise means for deterring said person from manually touching said face. In some embodiments said means for limiting comprise: a hinge having first and second wings rotatively joined at a fulcrum point, said first wing being secured to a forearm of said person, said second wing being secured to an upper arm of said person, and said fulcrum point being placed over an antecubital fossa between said forearm and upper arm; and means for restricting the range of rotation of said hinge. In some embodiments said means for limiting comprise: a hinge having first and second wings rotatively joined at a fulcrum point; said first wing being secured to a forearm of said person, said second wing being secured to an upper arm of said person, and said fulcrum point being placed over an antecubital fossa between said forearm and upper arm; means for restricting the range of rotation of said hinge; wherein, said means for deterring comprise: an E.M.R. emitter and an E.M.R. detector mounted on alternate ones of said wings; and means for signaling to said person when said detector senses a given E.M.R. level from said emitter. In some embodiments said means for signaling comprise a sensory stimulus element selected from the group consisting of: an audible signal generator; an electrical shock generator; and, a visual indicator. In some embodiments said means for limiting comprise a resiliently compressible member placed over the antecubital fossa of said arm. In some embodiments said member comprises a hermetically sealed and inflated bladder. In some embodiments said means for deterring comprise: a proximity sensor between said hand and said face; and means responsive to said sensor for signaling said person when said hand approaches said face. In some embodiments said means for signaling comprise a pain-inducing mechanism.

Some embodiments provide a device for warning a person that one of said person's hands is about to touch said person's face, which comprises a proximity sensor and a signal generator responsive to said detector. In some embodiments said proximity sensor is mounted proximal said person's face.

Some embodiments provide a device for signaling to a person that one of said person's hands is about to touch said person's face, which comprises a position sensor mounted on one of said person's forearms. In some embodiments said sensor is positioned to detect a substantially vertical orientation of said forearm. In some embodiments said sensor comprises a face to palm proximity detector.

Some embodiments provide a device for signaling to a person that one of said person's hands is about to touch said person's face, which comprises: a sleeve shaped and dimensioned to fit over the upper part of one each of said person's forearm, elbow and lower part of arm; a cable anchored at one end to said upper part and at an opposite end to said lower part, and passing behind said elbow; and means for detecting tension of said cable.

Some embodiments provide a device for minimizing the absorption of pathogens by a person through contact of said person's face by said person's hand, which comprises: a first activatable sensory stimulus element; a second activatable sensory stimulus element; a detector adapted to detect two or more orientation conditions of said hand; and a trigger responsive to said detector, said trigger being adapted to selectively activate said first and second elements. In some embodiments said orientation conditions comprise an event selected from the group consisting of: a relative location between said hand and said face being less than a first given distance; a relative location between said hand and said face being less than a first given distance for a given time period; and, a relative location between said hand and said face being less than a second given distance which is less than said first given distance.

Some embodiments provide a method for minimizing the absorption of pathogens by a person through contact between said person's hands and said person's face which comprises the step placing in the antecubital fossa of each of said person's arms an object shaped and sized to limit the range of movement of said hands toward said face. In some embodiments the method further comprises the step of: sensing the flexion of said arm about said fossa; and signaling to said person when said flexion reaches a given level. In some embodiments said signaling comprises emitting an audible signal. In some embodiments said signaling comprises applying a sensory stimulus to a part of said person's body. In some embodiments the method further comprises: in a second subsequent phase, removing said object; whereby said flexion is no longer limited, but said person is warned of an impeding contact between hand and face. In some embodiments the method further comprises, in a subsequent third phase, eliminating said signaling, and installing into said fossa a compressible member shaped and sized to apply a light pressure against said fossa upon said flexion without limiting the range of said flexion. In some embodiments the method further comprises: in a first phase, performing said limiting and said sensing steps; and in a second phase, eliminating said limiting and said sensing steps; and installing into said fossa a compressible member shaped and sized to apply a light pressure against said fossa upon said flexion without limiting the range of said flexion. In some embodiments the method further comprises progressively reducing said intensity over a period of time.

In some embodiments there is provided a method for minimizing the absorption of pathogens by a person through contact between said person's hands and said person's face, which comprises: sensing one of said hands approaching said face; and in response to said sensing, signaling said person that one of said hand approaches said face. In some embodiments said sensing comprises applying a sensory stimulus of a given intensity to a part of said person's body. In some embodiments said method further comprises progressively reducing said intensity over a period of time.

BRIEF DESCRIPTION OF THE DRAWING

FIG. 1 illustrates a person equipped with a variety of hand-to-face avoidance devices.

FIG. 2 is a diagrammatic perspective view of a first type of elbow flexion limiting device.

FIG. 3 is a diagrammatic perspective view of a first alternate version thereof.

FIG. 4 is a diagrammatic side view of a modified version of the device of FIG. 2.

FIG. 5 is a diagrammatic perspective view of an elbow flexion signaling device.

FIG. 6 is a diagrammatic perspective view of another embodiment thereof.

DESCRIPTION OF THE PREFERRED EMBODIMENTS

Figure 7:
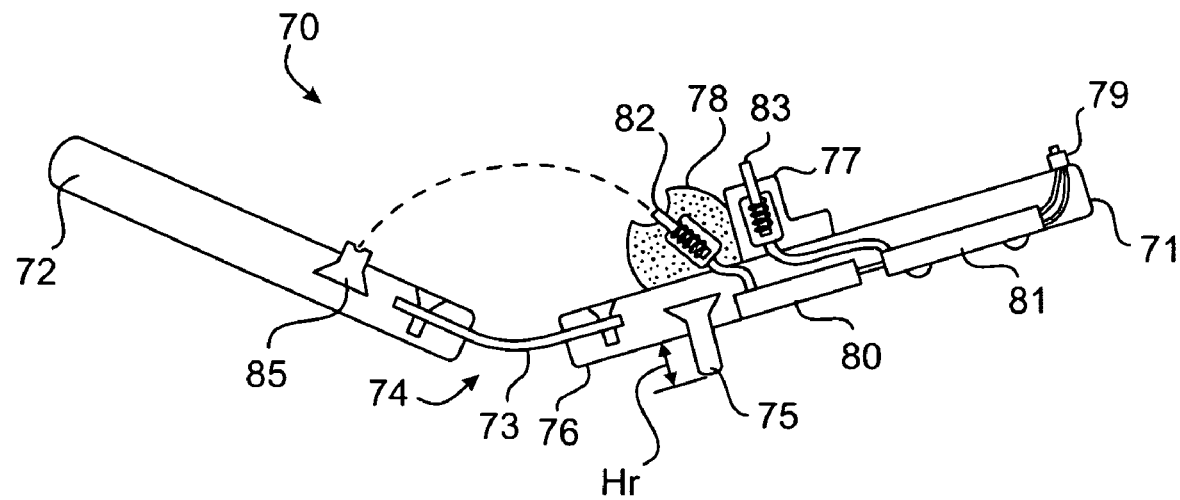
FIG. 7 is a diagrammatic partial cross-sectional side view of another embodiment thereof.

Referring now to the drawing, there is shown in FIG. 1, a person 1 equipped with a variety of devices 2, 3 and 4 intended to minimize the absorption of pathogens through contact of said person's face by one of said person's hands by heightening his or her awareness that the hand is in close proximity to the face. Two of the devices 2, 3 are designed to limit the range of movement of the person's hands toward the face. More specifically, the devices limit the degree of flexion of the elbows to approximately 135 degrees from full extension of the arm and forearm.

The first device 2, more specifically illustrated in FIG. 2, comprises a hinge having two wings 5, 6 rotatively joined at a fulcrum point 7. The fulcrum point is placed over the antecubital fossa, i.e., in the crook of the person's elbow. A first wing 5 is secured to the upper arm 8 by a strap 9, and the second wing 6 is secured to the forearm 10 by a similar strap 11. A barrier 12 mounted on the first wing 5 and projecting toward the second wing 6 prevents the wings from folding flatly against each other, and consequently, limits the flexion of the elbow. When folded to a point where the barrier 12 contacts the second wing 6, the hand at the end of the forearm 10 cannot be made to touch the face of the person without extensive and deliberate rotation of the person's shoulder. In other words, the device limits the swinging or hinge-like movement of the arm, thereby enabling the person to freely move his arm in a natural way up to a predetermined point where further movement is limited so that the person is made aware of the position of the hand, and in most instances cannot touch the face without assuming a forced, cramped, uncomfortable or otherwise unnatural position. Accordingly, the person will be deterred and trained from bringing the hand, which may have been contaminated by contact with a door knob or the like, in contact with the face where infectious pathogens transferred thereupon could be easily absorbed through the mouth, the eyes or the nose.

A pair of cooperating electromagnetic radiation (E.M.R.) emitter and detector 13, 14 are mounted on alternate ones of said two wings, 5, 6. A signal is generated when the detector senses a given E.M.R. level, indicating that the emitter and detector have come into close proximity of each other. Alternately, a momentary "on" push button switch can be located to be activated as the wings are brought together. The generated signal may be used to generate a warning from one or more types of sensory stimulus elements such as a visual indicator, an audio signal generator, a vibrator, or other sensory stimulus element 15 mounted on a wristband 16. The audio signal generator can include a volume adjustment to minimize noise interference with others. Alternately, or in addition to such a warning element, a wristband may include electrodes 25 in contact with the skin that can generate and discharge a mild electric warning shock to the arm. Such a shock or mild pain-inducing, or other negatively reinforcing event causing mechanism can also be mounted in the back of any of the disclosed devices. Upon experiencing the unnatural or unpleasant sensation, the person is discouraged from continuing the behavior. In this way, there can be a more rapid training of the person since awareness is heightened or the negatively reinforcing event occurs soon after or contemporaneously with the occurrence of the unwanted behavior.

The alternate embodiment of the flexion limiting device 3 illustrated in FIG. 3, comprises a sealed and inflatable bladder 17 made of two pouches 18, 19 joined by a flexible, constricted median section 20. The device acts essentially like the earlier described hinge 2. Each section of the bladder is secured to either the forearm or upper arm so that the median flexible portion 20 is located over the antecubital fossa of an elbow. The bladder 17 is inflated in order to provide a resiliently compressible barrier that resists flexion of the elbow. Visible through a cutout in the drawing, a pressure sensitive vibrator 22 is used to warn the person that the face is about to be contacted by the hand.

The third contact-deterring device 4 is a proximity sensor that can provide a signal when approached by one of the person's hands. Such a sensor is preferably worn on a chain 23 hanging from the person's neck. The sensor may be of the doppler radar type which detects the echo of radio frequency waveforms. It could also respond to the detection of E.M.Rs. generated by an emitter 24 mounted on the person's wrist.

The emitter and proximity sensor may be of the type described in U.S. Pat. No. 6,762,687, which patent is incorporated herein by this reference, or any other type well-known to the art.

Illustrated in FIG. 4 is a modified version 40 of the hinged device of FIG. 2 in which a bar 41 of elastomeric material is secured to the inner face of one of the hinge wings. The bar can comprise three coaxial layers 42,43,44 of material of different hardness in order to offer three stepped levels of resistance to compression. As the arm is folded beyond the angle A, the compression of the bar 41 offers increasing resistance to the folding movement. The wearer is thus warned that his hand may be moving toward his face. Further, the bar 41 can be removably fastened to the wing by a tongue-in-groove or other type fastener 45 so that a number of bars, each having a different uniform hardness, different layered hardnesses, and/or different sizes can be provided as a kit. In this way, the hinged device can be adjusted to allow greater freedom of movement as the course of training progresses.

Another type of embodiment 48 of elbow flexion signaling device is shown in FIG. 5. A cable 49 is imbedded into a sleeve 50 made of fabric or other stretchable material. The sleeve is shaped and dimensioned to fit over the elbow. The cable is preferably slidingly constrained within a flexible channel or tube 51 running along the back of the elbow. The cable is anchored at a first end 52 to the part of the sleeve covering the upper section of the forearm and at the opposite end 53 to the part of the sleeve associated with the lower section of the arm. A strain gauge 54 or other type of stain transducer connected to the cable provides a signal proportional to the degree of elbow flexion. Alternately, one end of the cable is secured to a normally open switch 55 at one of the cable anchor points. Flexion of the elbow causes a closure of the switch applying power to an indicator. A coil spring 56 is mounted in series with the cable in order to absorb any excessive pull on the switch or strain gauge.

Yet another embodiment 60 of elbow flexion monitoring device is illustrated in FIG. 6. An orientation or tilt sensor 61 mounted on a cuff 62 worn around the wrist or forearm, provides a signal when the forearm is brought to a substantially vertical position. Such a sensor can be implemented with a Series 3004 tilt switch manufactured by SIGNAL SYSTEMS CORPORATION and commercially available from JAMECO ELECTRONICS of Belmont, Calif. A directional E.M.F. emitter 63 mounted on the inner side of the forearm works in cooperation with the a detector such as the one 14 shown in FIG. 2, to indicate that the palm of the hand 64 is turned toward the face 65 and about to come into contact with it. The output signals of the tilt and proximity sensors can be used singly or in combination to generate a warning indication.

FIG. 6 also illustrates the packaging of the device shown in FIG. 2 in a pouch 66 associated with an elbow sleeve 67 of the type illustrated in FIG. 5. Alternately, a cinchable cuff of the type used in connection with a sphygmomanometer may be substituted for the sleeve.

Yet another embodiment of elbow flexion monitoring device is illustrated in FIG. 7 which shows that a single device 70 can be adapted to carry a number of different types of activatable and deactivatable sensory stimuli elements. The device is similar to the hinged device of FIG. 4 by providing two wings 71, 72 bonded to opposite ends of a flexible web 73 thereby rotatively joining the wings at a fulcrum point 74. A removable positioning rib 75 can be fastened to project from a outer face 76 of the first proximal wing 71 to engage the antecubital fossa to help prevent migration of the device in persons having well developed musculature. A number of ribs having different heights Hr can be provided in a kit allowing adaptation of the hinge device to suit different anatomies. The rib can be removably fastened to the wing by means of a tongue-in-groove type fastener.

A barrier 77 mounted on the inner face of the first wing 71 and projecting toward the second distal wing 72 prevents the wings from folding flatly against each other, thereby limiting flexion. A bar 78 of elastomeric material is secured to the inner face of the proximal wing 71 against the barrier to provide a stepped level of resistance to compression. A multi-poled activation switch 79 configures the device by activating one or more of the stimulus-causing elements such as a vibrator 80 and mild electric shock generator 81. A pair of momentary "on" push button switches 82,83 are located to be actuated at different angular positions between the two wings. Further, a first one of the switches 82 can be positioned within the elastomeric bar so that it is actuated after contact between the second wing 72 and the bar 78 has occurred. Alternately, a removable switch actuating extension prong 85 can be provided to adjust the angle at witch the switch 82 is actuated. The second switch 83 can be formed into the barrier 77 and located to be actuated at a given angular orientation of the wings.

In this way, the device can be configured to provide increasingly unpleasant stimuli as the angle between the wings is reduced. For example, at a first acute angle the person feels a flexion resistance when the elastomeric bar is compressed. At an even smaller angle, the vibrator is turned on, and at even a smaller angle the person receives a mild electric shock.

Further, a timer circuit can be used to delay the onset of the vibration or shock stimuli until the switch has been on over a threshold period of time. Alternately, for example, the electric shock generator can be configured to never activate if the person does not require such an unpleasant stimulus. Those skilled in the art will appreciate the implementation of these functions through electronic circuitry and including the use of microprocessors.

Further, the switches 82,83 and the physical size, shape and location of the bar 78 act as orientation detectors adapted to detect two or more orientation conditions of the user's hand and trigger two different stimuli. It should be noted that such conditions can be events such as the location of the user's hand being within a given distance of the face as measured by the angle formed between the wings, and the first stimulus would be the sensation of pressure or a limiting of movement caused by the bar 78 contacting the opposite wing 72. This condition may have already turned on switch 82. A second orientation condition or event could be the wings remaining at the same angle and the hand remaining at the same distance from the face, but that a sufficient time period has passed as measured by a microelectronic clock started at the time switch 82 was turned on. Another orientation condition event could be the wings being brought further together to activate switch 83 causing an immediate mild electric shock.

A combination of the above-described devices can be advantageously used in correcting a person's tendency to inadvertently touch his or her face. In a first phase lasting a short period of time, one of the flexion restrictive devices 2, 3 is used along with one or more of the proximity sensor 14 and, optionally, a signaling element or sensory stimulus element, such as a pressure increasing element, vibration, mild shock after a timed duration, or visual indicator 15. In a subsequent, second phase, the restrictive device is removed. The proximity sensor and indicator may be kept or a small flexion-resisting device, such as the partially deflated bladder device 3, is worn by the person. The flexion-resisting device is sized or inflated so that it does not interfere with the full flexion of the elbow, but exerts enough pressure on the arm and forearm to make the person aware that the hand may be approaching the face.

It should be understood that the intensity of the sensory stimulus triggered by the above-described devices can be made proportional to the degree of elbow flexion or the proximity of the hand to the face. While a person may initially react to a high level of stimulus, he will eventually become responsive to a lower level. Accordingly, the intensity of the stimulus is preferably adjustable by means of a rheostat or other amplitude-controlling implement. As the person eventually becomes more sensitized to the stimulus, the intensity is progressively reduced over a period of time until the compulsive face-touching habit disappears and the device is no longer needed.

In an optional, subsequent third phase, only the flexion-resisting device is used until the person has completely overcome his or her face-touching habit.

While the preferred embodiments of the invention have been described, modifications can be made and other embodiments may be devised without departing from the spirit of the invention and the scope of the appended claims.

What is claimed is:

1. A method for minimizing the absorption of pathogens by a person through contact between said person's hands and said person's face, which comprises:
    selecting a hand location detection and signaling apparatus;
    detecting with said apparatus a first orientation condition of one of said hands;
    detecting with said apparatus a second orientation condition of said one of said hands, different from said first condition;
    applying a first sensory stimulus with said apparatus to said person during said first condition; and,
    applying a second sensory stimulus with said apparatus to said person during said second condition;
    wherein said first and second stimuli are different from each other.

2. The method of claim 1, wherein said first sensory stimulus has a first given intensity, and wherein said second sensory stimulus has a second given intensity different from said first given intensity.

3. The method of claim 2, which further comprises progressively reducing said first given intensity over a period of time.

4. The method of claim 1, wherein said applying a first sensory stimulus comprises emitting an audible signal.

5. The method of claim 1, wherein said detecting a first orientation condition comprises:
    sensing the flexion of each of said person's arms about each of said arms' antecubital fossa; and,
    signaling to said person when said flexion reaches a given level.

6. The method of claim 5, which further comprises the step of placing in the antecubital fossa of each of said person's arms an object shaped and sized to limit the range of movement of each of said hands toward said face; and limiting the range of movement of said hands.

7. The method of claim 6, which further comprises:
    in a second subsequent phase, removing said object;
    whereby said flexion is no longer limited, but said person is warned of an impending contact between hand and face.

8. The method of claim 7, which further comprises, in a subsequent third phase, eliminating said signaling, and installing into said fossa a compressible member shaped and sized to apply a light pressure against said fossa upon said flexion without limiting the range of said flexion.

9. The method of claim 6, which further comprises:
    in a first phase, performing said limiting and said sensing steps; and
    in a second phase, eliminating said limiting and said sensing steps; and
    installing into said fossa a compressible member shaped and sized to apply a light pressure against said fossa upon said flexion without limiting the range of said flexion.

10. The method of claim 1, which further comprises:
    wherein said second orientation condition differs from said first orientation condition by the amount of time said one of said hands remains within a given distance of said face.

11. The method of claim 10, which further comprises:
    stopping said second sensory stimulus when said one of said hands moves beyond said given distance.

12. The method of claim 2, wherein the intensity of said first stimulus is proportional to a decrease in distance between said one of said hands and said face.

13. The method of claim 1, wherein one of said first and second sensory stimuli is selected from the group consisting of:
    applying a change in pressure against said person;
    applying a vibration to said person;
    applying a mild electric shock to said person;
    generating an audible sound; and
    activating a visual indicator.

\* \* \* \* \*